US00PP35727P2

(12) United States Plant Patent
DeJong et al.

(10) Patent No.: US PP35,727 P2
(45) Date of Patent: Apr. 9, 2024

(54) PRUNE TREE NAMED 'UC G2S-8'

(50) Latin Name: *Prunus domestica*
Varietal Denomination: UC G2S-8

(71) Applicant: The Regents of the University of California, Oakland, CA (US)

(72) Inventors: Theodore M. DeJong, Davis, CA (US); Sarah Castro, Elk Grove, CA (US); James F. Doyle, Clovis, CA (US); Carolyn DeBuse, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/445,112

(22) Filed: Apr. 12, 2023

(51) Int. Cl.
*A01H 5/08* (2018.01)
*A01H 6/74* (2018.01)

(52) U.S. Cl.
USPC ..... Plt./185
CPC ..... *A01H 6/7472* (2018.05)

(58) Field of Classification Search
USPC ..... Plt./185
CPC ..... A01H 6/7472; A01H 6/7427; A01H 5/08
See application file for complete search history.

(56) References Cited

PUBLICATIONS

Castro et al., "Developing new prune cultivars for the California dried prune industry," Acta Hortic, 2021, vol. 1322, XII International Symposium on Plum and Prune Genetics, Breeding and Pomology, pp. 13-18.

*Primary Examiner* — Keith O. Robinson
(74) *Attorney, Agent, or Firm* — McKee, Voorhees & Sease, PLC

(57) ABSTRACT

A new prune cultivar designated 'UC G2S-8' has been developed. The fruit of this cultivar are medium, yellow in color and covered with a grayish waxy bloom. The 'UC G2S-8' tree is productive and a regular bearer.

6 Drawing Sheets

Botanical designation:
Botanical/commercial classification: *Prunus domestica*/ "French-type" prune variety.
Variety denomination
Varietal denomination: cv. UC G2S-8.

BACKGROUND

Prunes are a popular food item providing a good source of vitamin C as well as other vitamins and nutrients for consumer digestive health. As such, there is a continued need to develop prune trees with increased yield and quality of plums for the production of prunes.

There is a tremendous need for developing new California prune varieties where the resulting trees express precocity of bearing (shortened juvenility), spread of maturity (both early and late), and fruit with easy processability.

SUMMARY

In order to meet these needs, the present disclosure is directed to the 'UC G2S-8' prune tree which is a new prune cultivar developed for the dried fruit market. It is of the plum species *Prunus domestica*. This new cultivar is the result of a controlled cross made between two University of California (UC) proprietary breeding program lines. The cross between '5-19-39' (not patented) and '6-15-62' (not patented) was made in Parlier, CA in March of 1999. The cross was made between the breeding item '5-19-39' used as the female (seed) parent and the plum cultivar '6-15-62' used as the male (pollen) parent. '5-19-39' was a result of an open-pollinated 'Burton' (not patented) seedling. '6-15-62' was a result of a cross between 'Improved French' (not patented) and '5-3-21' (not patented), a UC breeding item. Hybrid seed harvested from '5-19-39' and '6-15-62' at the end of the 1999 growing season was given the family designation "2000.12.05". The family was germinated at UC Davis, then grown into small bare-root trees along with other families at a nursery in Loomis, CA. The family of 71 was then planted in the "G block", an orchard designated for seedlings at UC Davis in early spring 2001. The seedling block was located within the pomology field research area at University of California, Davis.

'UC G2S-8' was first harvested from the original seedling in August of 2007. The first propagation of selection 'G2S-8' occurred in April of 2008 into prune selection blocks in Winters, CA. and Parlier, CA. These propagations involved grafting onto second year 'Marianna 2624' (not patented) rootstock in Winters, CA, and 'M40' (U.S. Plant Pat. No. 11,403) rootstock in Parlier, CA. In 2015, 34 nursery budded trees were planted on 'Myrobalan 29c' (not patented) rootstock in Winters, CA. These experimental trees came into full bearing in the summer of 2019. In 2019, 2020, 2021, and 2022, fruit from 31 trees were commercially shaken and the fruit dried, and processed in commercial settings. The resulting processed fruit was tasted in various settings. From seedling to selection blocks in Winters, CA and Parlier, CA, propagation was performed via top grafting (bark grafts) about 90 cm from the ground on $2^{nd}$ leaf rootstock in the spring. Subsequent propagations were performed via budding at a traditional tree nursery under a confidential/non-commercial test agreement. Asexual propagation of the cultivar by grafting and budding has determined that the characteristics are stable and true to type in successive generations.

The 'UC G2S-8' tree is similarly vigorous to the standard 'Improved French', it is productive and is a regular bearer. The 'UC G2S-8' prune has been successfully propagated on 'Marianna' plum rootstock with good results, however, it is not recommended that it be grafted on peach rootstocks without significant pre-testing as many other *Prunus domestica* cultivars are incompatible with peach. Fruit of the 'UC G2S-8' cultivar dries into a very high-quality prune with an excellent, fruity flavor. The fresh fruit skin is yellow, but the dried product's color is deep mahogany that after processing darkens to resemble the same color as the standard California prune.

'UC G2S-1' matures 1-2 weeks after seed parent '5-19-39', pollen parent '6-15-62', and industry standard 'Improved French'. In further comparison, 'UC G2S-1' has large, yellow fruit, whereas '5-19-39' has large, purple fruit with a yellow blush and '6-15-62' has medium, purple-red fruit.

BRIEF DESCRIPTION OF THE PHOTOGRAPHS

DETAILED BOTANICAL DESCRIPTION

Figure 1:
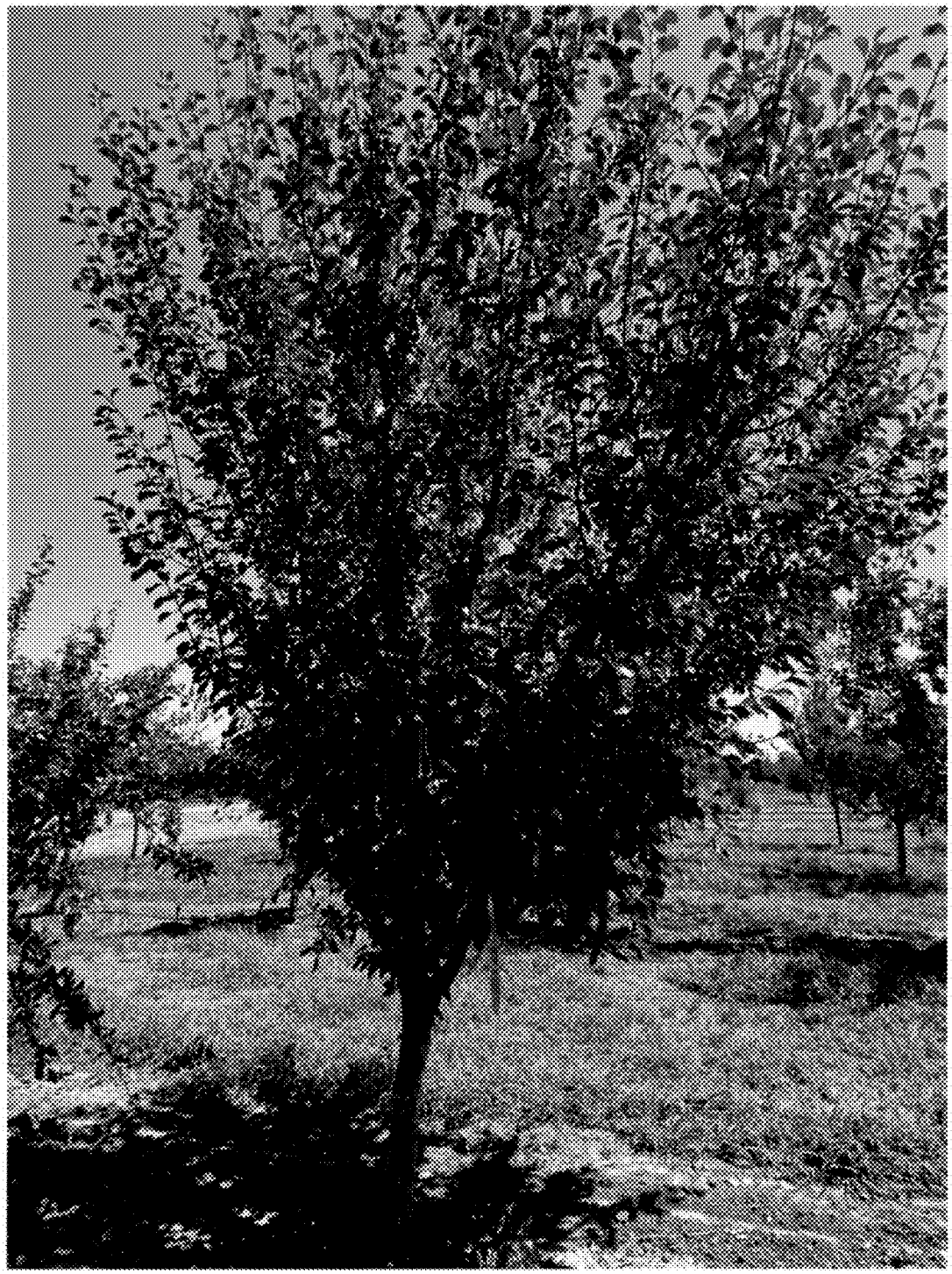
FIG. 1 is a photograph of a five-year-old 'UC G2S-8' prune tree in the summer with fruit taken in July 2020 at UC Davis.
Figure 2:
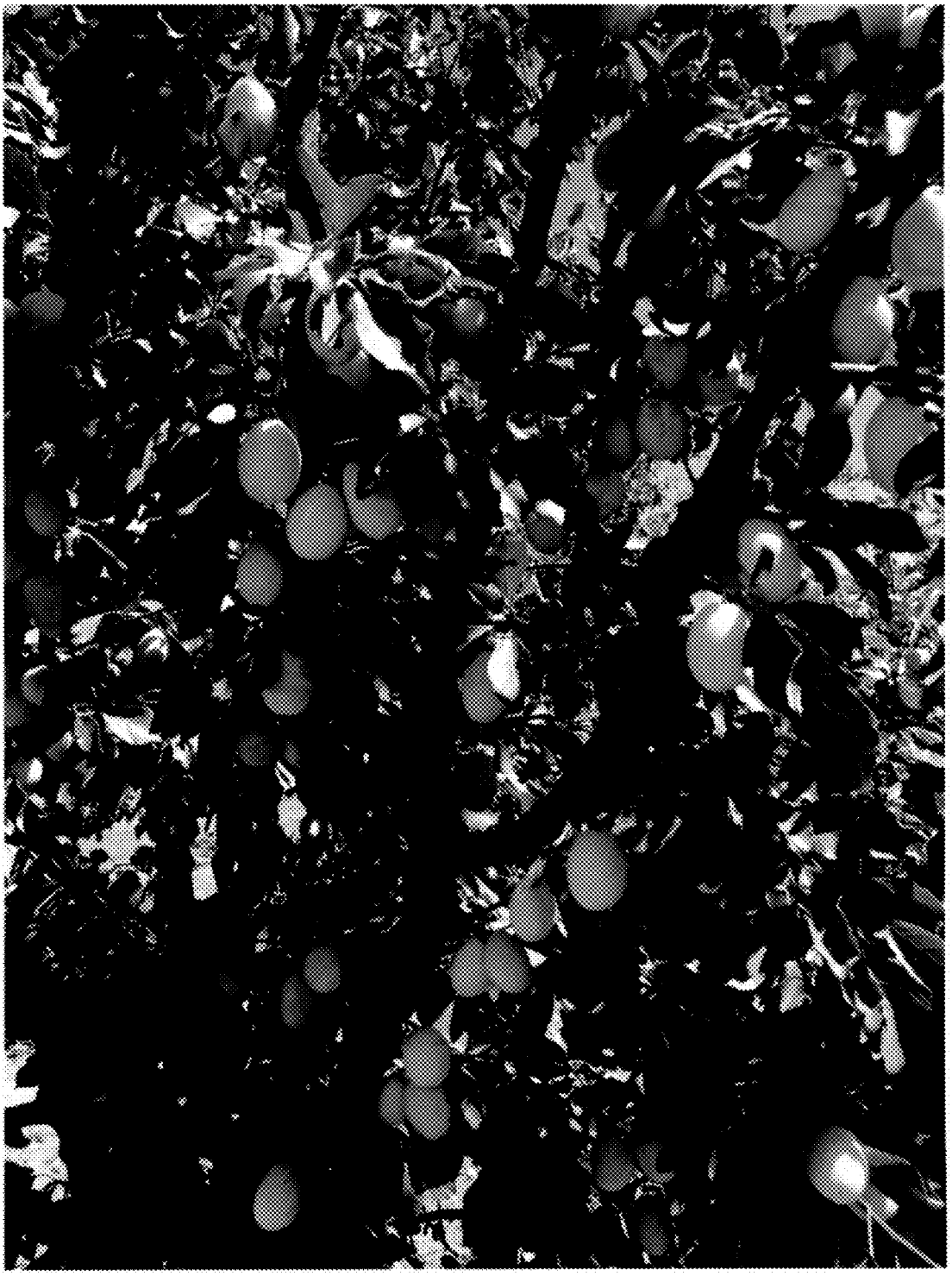
FIG. 2 is a photograph of 'UC G2S-8' fruit on a five-year-old tree near harvest time taken in 2019 at UC Davis.
Figure 3:
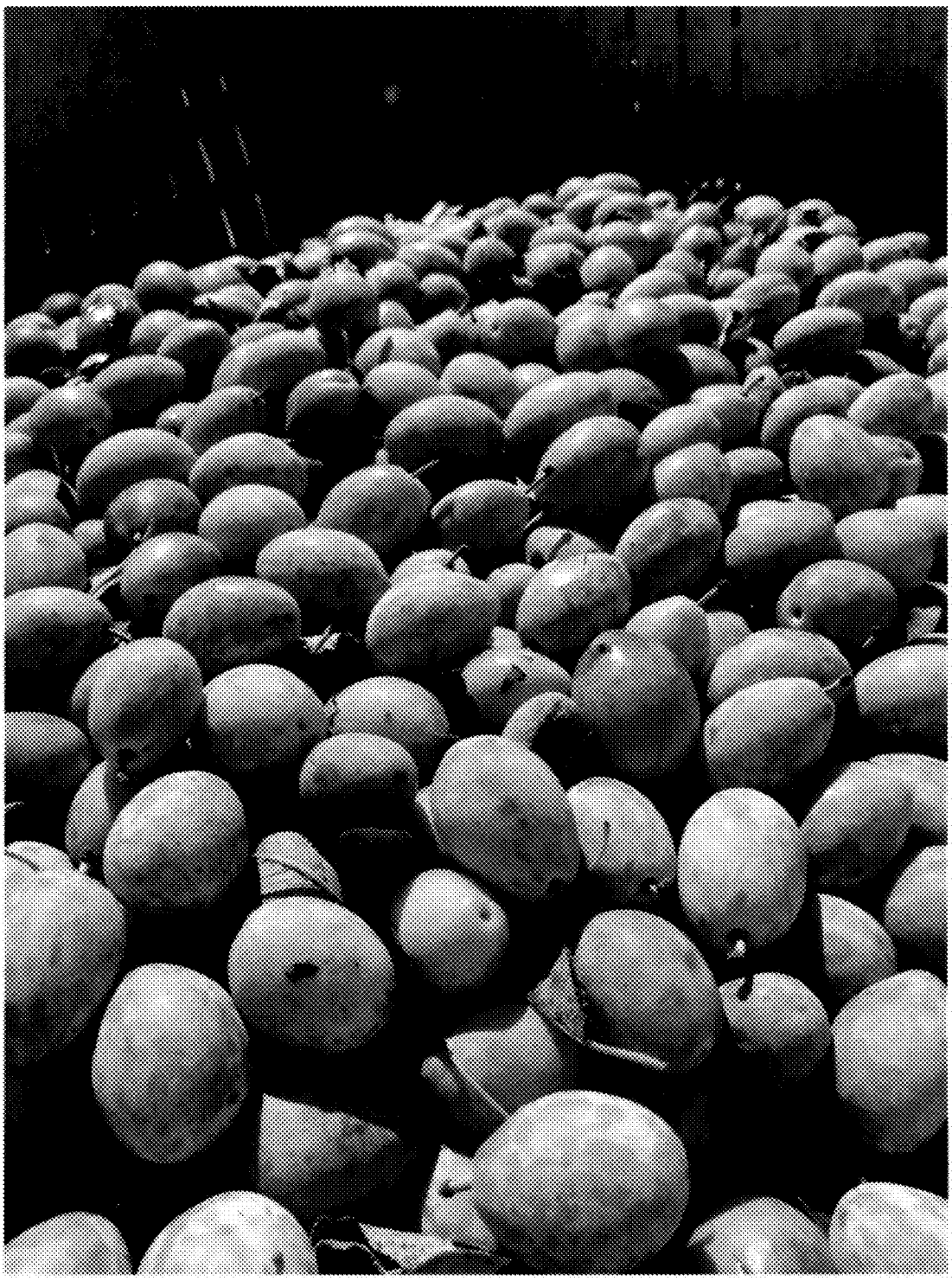
FIG. 3 is a photograph of 'UC G2S-8' fruit in a bulk bin after mechanical harvest taken in February 2023.
Figure 4:
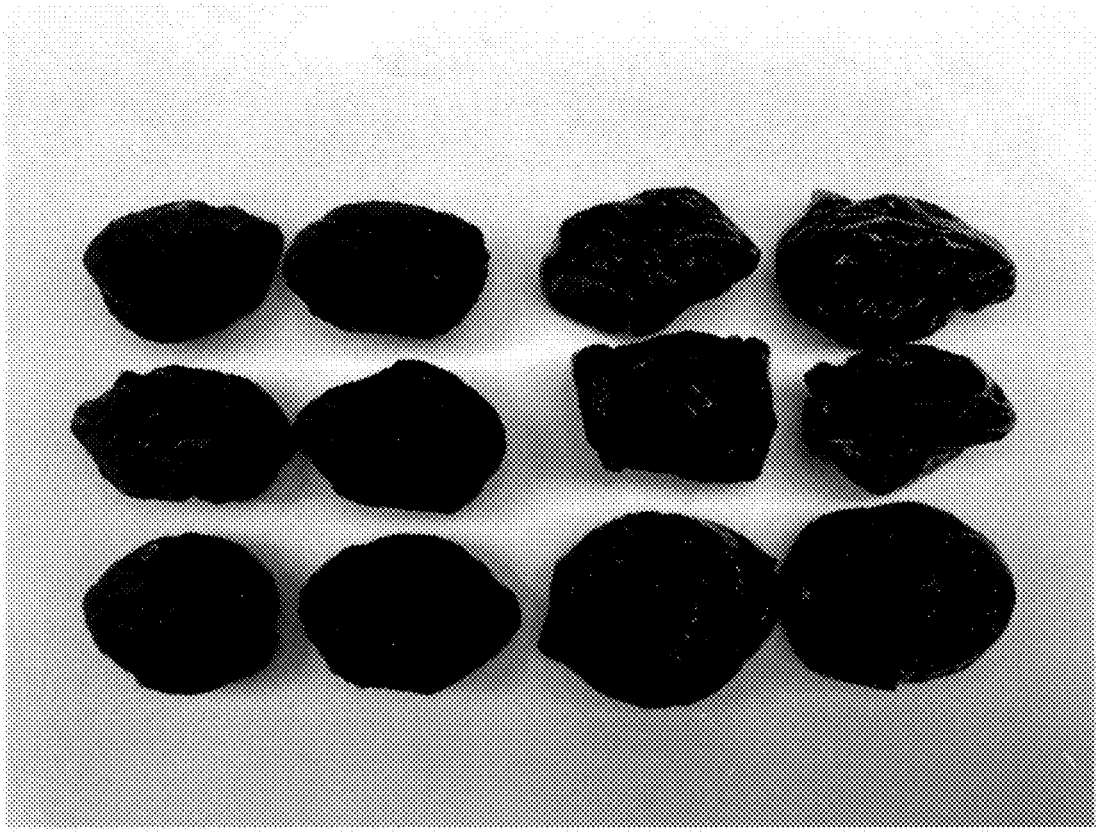
FIG. 4 is a photograph of 'UC G2S-8' fruit after drying in "natural condition" (left) taken in and after processing (rehydrated, pitted and treated with potassium sorbate) (right) taken in September 2022.
Figure 5:
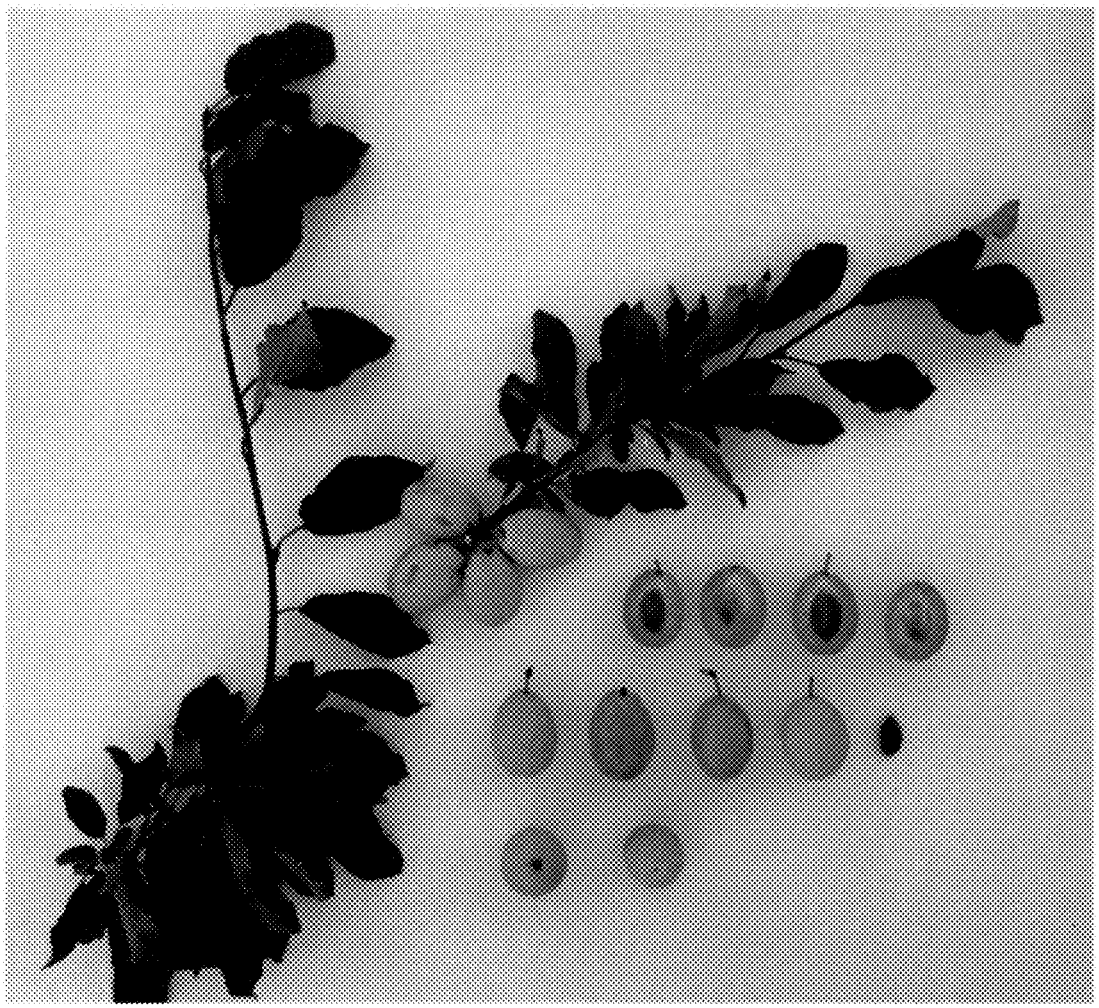
FIG. 5 is a photograph of 'UC G2S-8' leaves and fruit taken in August 2019.
Figure 6:
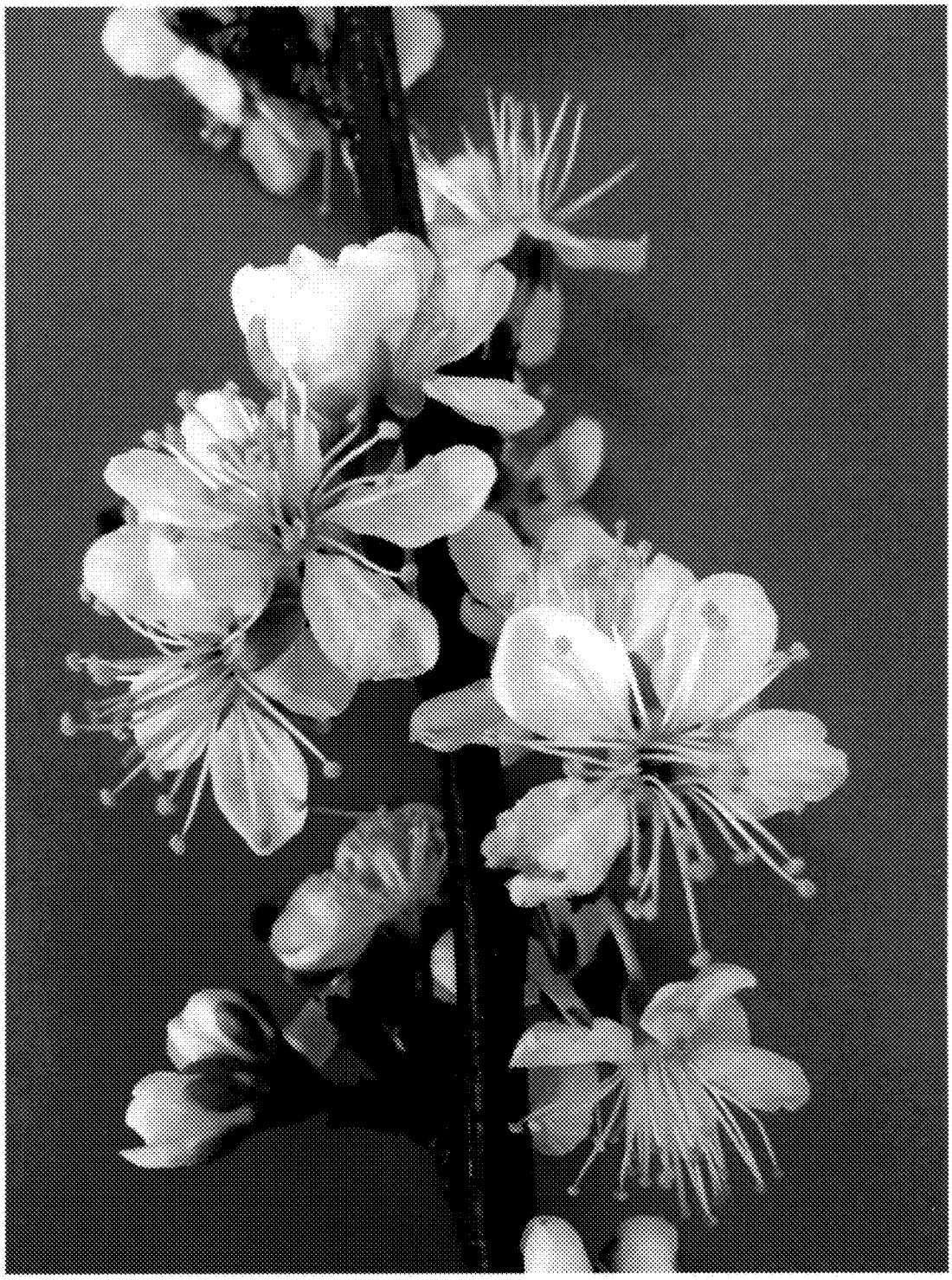
FIG. 6 is a photograph of 'UC G2S-8' flowers taken in February 2023.

The following horticultural description was prepared from plant material and fruit obtained from fully grown nursery budded trees on 'Myrobalan 29c' rootstock. The plant material was observed during the 2019 and 2020 growing seasons in Winters, CA. Descriptions are provided below. Color definitions used in this description are from the "Dictionary of Color" by Maerz and Paul, First Edition (1930).

Tree: The genus and species of the subject new cultivar is *Prunus domestica*. This species is popularly known as "European plum". Individual cultivars of this plum species that are high in sugar content and can dry without fermentation have historically been designated as "prunes". The tree of the subject new cultivar is average in vigor and hardy under normal Sacramento Valley, Calif climatic conditions. Tree form is upright to upright-spreading. The trees have been maintained by pruning in an open-vase training system. Trees detailed in this document were $5^{th}$-year nursery budded trees on 'Myrobalan 29c' rootstock. Trees are tall and upright ranging from 12-20 feet tall. In general, this tree bears wood similar to 'Improved French' where there are sparsely spaced spurs of varying lengths but can also bear on vigorous one-year-old shoots. Some spurs are compact, and others are a longer, hanging form. Nursery budded trees have been producing fruit for at least 5 years. Every year there has been an adequate to excellent crop. In 2020 and 2021 the trees needed to be shaker thinned to maintain tree health and to attain good fruit size.

Trunk: On a 5-year-old, nursery budded tree, the union was 5 cm off the ground. Below the union 2 cm, the 29c rootstock section measured 35.3 cm in circumference, and 20 cm above the union measured 32.2 cm in circumference. The surface texture of the trunk is moderately roughened. The color of the trunk is Plate 8 E-1 with gray highlights. The trunk lenticels are mostly 7.5-12 mm, but can get as short or as long as 6 to 24 mm. The color of the trunk lenticels are Plate 8, H-8, and A-7.

Branches: On the 5-year-old tree, there were 4 scaffolds off the main trunk, they ranged from 27.3-19.0 cm in circumference. Each had 1-3 secondary scaffolds which had a color of Plate 8 E-7 with gray highlights. The lenticels on the scaffolds were 2.5-6 mm in length. On more medium-sized branches where the wood is only 2 or 3 years old, there are typically 11 lenticels in a 1.8 $cm^2$ section. The lenticels are close to old burgundy in color, Plate 56 H-10. On immature wood, the upward side of the stem is 75% red in color (Plate 7 H-3) and 25% on the underside of the stem is green (Plate 15 L-1).

Leaves: Leaves in general are shiny as compared to the standard 'Improved French' cultivar. The leaf surface is slightly rugose. Leaf thickness is average, with a defined midvein that contrasts in color nicely to the dark green leaf blades. The shape of the leaf blade is ovate from base to tip. The ovate shape is typically wider at the base of the leaf blade.

*Leaf form*.—The oval leaf sizes are medium to small with wide leaves on new growth and narrower leaves on short spurs. The longest leaves were 73 mm in length and width were 46-50 mm. The leaves growing off of spurs tend to be narrower, almost narrow elliptic, in shape. The ratio of length/width was 1.8-2.1.

*Leaf color*.—The upwardly disposed surface of leaves are cypress green, Plate 23 L-6 and the downwardly disposed surfaces were closer to a garland green, Plate 22 F-6.

*Leaf margins*.—Leaf margin form is crenate. The crenations can be irregular and sometimes double crenate. The leaf margins can be slightly undulate. The leaf veins are fairly distinct when viewed from the upper part of the leaf. The vein color is almost courge green, Plate 21 K-3.

*Glandular characteristics*.—The glands are sometimes grown from the petiole, others are growing from the leaf margin. They tend to be red or green, the red are Plate 7 J-9 and others that are green are similar to the vein color, Plate 21 K-3.

*Leaf petiole*.—The leaf petiole is average size. It can range from 0.7 to 1.1 mm diameter with the length ranging from 13-22.5 mm. It is a green color, Plate 21 K-3.

*Leaf stipules*.—The leaf stipules are upright, vigorous growth tends to have 3-4 stipules per node. They are thin and range from 2 mm-6.5 mm in length. They can abscise as the new growth matures through the season.

Floral description: The following floral description was obtained from plant material growing on test trees of the 'UC G2S-8' cultivar located in Winters, California. This description was developed during March of 2020. The number of cold chilling hours (total hours below 45 degrees F.) for the 2019 chilling year was 799 hours. This accumulation is lower than an average year. The number of cold hours accumulated for the 2014 chilling year and the 2016 chilling year were 1010 and 1028, respectively. The 2014 and 2016 years represent relatively cold winters. Because of the similarity of dates of bloom for the 'UC G2S-8' cultivar in all years, it appears that the chilling requirement of the 'UC G2S-8' cultivar was fully satisfied at both levels of chilling.

*Flower buds*.—Size and Surface: The flower buds range from medium to large in size. They are conic and range from 2 to 3.5 mm in length and from 1 to 2 mm in width. The surface of the bud scales are mostly glabrous, with the margins having a slight serration. Form and Color: General bud form is slightly variable but most frequently conic and plump. The buds most often are moderately appressed to the bearing branch. The flower buds are hardy under the normal climatic conditions that occur in the Sacramento Valley of Central California. Bud color is a dark brown (Plate 8 J-7).

*Bloom timing*.—Bloom timing for 'UC G2S-8' is typically late in the second week of March. In March of 2020, the tree bloomed on March 11$^{th}$. In relation to the industry standard, 'UC G2S-8' blooms 4.8 days before 'Improved French' (n=10). This of course can be variable depending on the environmental conditions that year. In 2014 specifically, there was only 593 chilling hours between 32-45 degrees F., this created a generally late bloom and 'UC G2S-8' bloomed 9 days before 'Improved French.'In 2020, 'UC G2S-8' was tested for its ability to self-pollinate. The tree was completely isolated from other trees using 30% shade cloth, then bumble bees were placed with the tree to insure pollen movement. After bloom was over and fruit set was documented, it had produced a medium crop and was therefore considered pollen self-compatible.

*Flower size*.—Flower size ranges from medium to large for the species. The diameter of the flower, fully expanded, varies from 23 to 27 mm.

*Bloom quantity*.—The quantity of bloom is abundant. The number of flower buds per node ranges from 1 to 2, most frequently 2. Within a bud, 1-3 flowers can be produced.

*Flower petals*.—Flower petals are medium to large in size. Petals range from 10 to 12 mm in length and from 7-9 mm in width and are slightly cupped. The petal number is five free petals. The petal form is variable, but mostly oval. Petal color is white (Plate 25 A-1). The petal claw is truncate in form and quite short. The petal margins are only slightly undulate and slightly cupped inwards. The margin can be loosely crenate at times. Petal apex is usually smooth and rounded.

*Flower pedicel*.—Pedicel length ranges from 7 to 12 mm. Pedicel thickness ranges from 0.8 to 1.5 mm measured at mid-pedicel. Color of the pedicel is Plate 21 K-4. The surface of the pedicel is glabrous.

*Floral nectaries*.—Color of the floral nectaries is a dull yellow-green (Plate 19 G-5).

*Calyx and sepals*.—Surfaces of the calyx are slightly pubescent, with extremely short hairs. The sepal surfaces are slightly pubescent, with very short and fine hairs, except along the sepal margins where the pubescence is more pronounced. The sepals are of average size, ranging from 4 to 5 mm in length and from 2 to 3 mm in width. The sepals are most frequently ovate in form and reflex back toward the pedicel. Sepal color is green (Plate 21 L-5).

*Anthers and pollen*.—The anthers are average to slightly above average in size, measuring slightly greater than 1 mm long and slightly less than 1 mm wide. Anther color is a gold- yellow (Plate 9 K-1). Pollen quantity is abundant, with at least 25 anthers per flower. The tree is self-fertile.

*Stamens*.—The stamens are variable in length, from 7 to 10 mm extended above the hypanthium. The stamens are usually shorter in length than the pistil. Filament color is white (Plate 33 A-1).

*Pistil*.—Pistil length ranges in length from 13 to 15 mm, including the ovary. The style is approximately 12 mm above the ovary, and the stigma is 1-2 mm above the anthers at maturity. The upper (distil) portion of the style is pale green in color (Plate 20 C-2). The basal portion of the style and the ovary are darker green (Plate 20 H-4). There is an absence of pubescence on the ovary. Often, when the flower bud has not yet opened, the stigma protrudes out above the anthers.

Fruit description: Color Reference used: Maerz, *A dictionary of Color* 1930.

*Date of maturity*.—Late August to early September, typically 7-14 days after 'Improved French'. In 2020, fruit was harvested on August 31$^{st}$ in Winters, CA.

*Fruit size*.—Generally medium to large with fairly uniform size. Individual fruit weight averaged 31.7 g on a tree with a moderate to heavy crop load. The diameter of the axial plane is 37-46 mm with an average of 41.7 mm. The transverse in suture plane is 30-36 mm with an average of 32.7 mm; and the transverse that is a right angle to suture plane is 27-35 mm with an average of 31.1 mm.

*Form*.—Form is oblong in shape, and can be slightly asymmetrical.

*Suture*.—The suture is visible, but not obvious, and is only slightly depressed.

*Stem*.—The stem cavity is round and typically 3 mm wide and 2 mm deep. The stem length averages 10 mm and ranges from 8-12 mm. The stem caliper averages 1.4 mm and ranges from 1-2 mm with an average of 1.4 mm.

*Skin*.—The skin thickness tends to be thin but durable. The texture is smooth with few instances of scab or blemish. The flavor is neutral and does not add much flavor to the overall taste of the fruit. The skin very rarely cracks, pre or postharvest. In general, the skin and flesh only have slight variations in color. The skin color has a ground color (waxy bloom removed) of Plate 10 1-2, some fruit that has had a lot of sun exposure have a slight blush on it creating a more daffodil Sunray color (Plate 10 J-6). With the bloom still on the skin the skin color is less vibrant Plate 10 B-3.

*Flesh*.—The flesh color is Plate 10 L-5, that gets slightly lighter in the pit well (Plate 10 E-3). The flesh flavor is very pleasing with an excellent fresh texture and sweetness. The flesh of the fruit is firm but becomes soft when the fruit is past maturity.

*Stone*.—The stone is mostly free with very few fibers present. Of 5 fruit, one fiber was present with a length of 3 mm. The size of the pit averages 22.3 mm in length (range 19-25 mm), 13.6 mm in width (range 12-15 mm), and 7.6 mm thick (range 6-11 mm). The apex shape is intermediate with a rounded base. The sides are moderately rough with two flat ridges seen at the ventral view. There is very little tendency for the pit to split before or after harvest. The dry color of the pit is Lariat colored (Plate 12 C-6).

*Maturity*.—The fruit of this new cultivar is described at full commercial maturity. Time of harvest in 2020 and 2021 was in the last week of August and first week of September, respectively in Winters, CA. This corresponded to the last days of harvest of the common 'Improved French' cultivar in both years. At the time of harvest fruit of 'UC G2S-8' had an average flesh pressure of 4.0 and an average soluble solids content of 28.2 degrees Brix in 2021 and in 2020 had 3.4 flesh pressure and 24.8 degrees Brix. In both years harvest was performed by mechanically shaking the fruit onto tarps. The fruit was subsequently dumped into bulk bins and trucked to commercial prune drying facilities. The fruit withstood all of this bulk handling with negligible damage.

*Eating quality*.—Eating quality of the 'UC G2S-8' fresh fruit is very good, especially when the sugar level reaches or exceeds 24 degrees Brix.

*Processing quality*.—With similar crop loads, the 'UC G2S-8' cultivar appears to develop larger sized fruit with higher fruit quality than that of the industry standard dried plum, the 'Improved French'. Fruit of the new cultivar dries into an attractive, high quality dried plum or prune but is distinctively different from 'Improved French' in flavor (sweeter) and color (dark brown vs. black). After bulk storage, the color of the dried fruit darkens to a color similar to the standard 'Improved French'. The fruit stone of the 'UC G2S-8' is essentially freestone and the dried fruit pits easily using the industry standard "Ashlock" mechanical putter as well as the proprietary "Sunsweet pitter". Dried flavor of the 'UC G2S-8' fruit is lighter and sweeter than that of the 'Improved French'.

*Resistance to pests and diseases*.—Unknown.

DETAILED DESCRIPTION

The breeding strategy of the program to develop the 'UC G2S-8' can be separated into four distinct phases each having an individual purpose and crossing method. The first phase involved progeny testing of prune cultivars which historically have shown adaptation to California growing conditions. Open-pollinated seedling populations derived from each cultivar were screened with the standard fruit evaluation and individuals were identified that expressed precocity of bearing (shortened juvenility), spread of maturity (both early and late), freedom from heat damage (in both fruit and tree) and vigorous seedling growth.

The superior seedlings from Phase 1 were advanced as parents into Phase 2 and Phase 3 hybridization. The purpose of the second phase was to increase the diversity of the germplasm by breeding cultivars that had positive characteristics but had not been used in California production. Superior seedlings possessing commercial cultivar characteristics could be identified at any point in this program. In Phase 3, 'Improved French' was being utilized as a common parent in a "backcross" breeding method. This phase used superior seedlings identified in Phase 1 and Phase 2 as parents and crossed them to a single common parent, 'Improved French'. This "backcross" breeding method generally produced seedling populations that contained at least 50% "French" genome and had a high potential for producing fruit similar to "French" on vigorous, precocious, and productive trees. The fourth phase of the breeding program involved further breeding and selection of the superior seedlings from Phases 2 and 3 that produced fruit with high fruit quality that could withstand commercial harvesting, drying, handling and pitting processes that were common in the industry.

Pollination and Seedling Cultivation

The annual workings of the breeding program began at pollination. A pollination list was planned by selecting the parents from the top selected items that showed the potential of becoming new cultivars and from the items that had been selected on their breeding potential but lacked the potential of becoming cultivars themselves. Flowers from the pollen parent were collected from the trees at the popcorn stage of bloom. The fully closed flowers were removed from the trees and the stamens were separated by rubbing the flowers over a clean screen. The stamens were dried at ambient temperature to release the pollen. The pollen was stored in vials in a refrigerator. Limbs of the seed parents are chosen for crossing when the flowers have reached 40-50% of full bloom. All of the open flowers were removed from the limbs and discarded. The remaining closed flowers were emasculated (petals and stamens were removed) with tweezers, leaving only the pistil and ovary attached to the tree. The collected pollen was placed on each individual pistil of the selected limbs. Five hundred to fifteen hundred flowers were pollinated for each desired cross to ensure a moderately sized progeny family. The large number of pollinations were needed because fruit set could be variable due to a variety of factors: poor weather, pollen non-viability, parental incompatibility, and manual damage. The fruits formed by the pollinations were left to mature on the tree until about 10 days before fruit ripening.

Seedling culture was the care of the seedlings from seed to nursery. The first step was the collection of the fruit from the pollinations. The fruit was stored at 32° F. until the time of seed removal. The seed was removed from the fruit in early fall and placed in plastic bags with moist paper towels that contained antibiotics and fungicide. The seed was then stratified for 2 months at 37-45° F. After stratification, the seed coats were peeled off each seed to remove any growth inhibitors that might still be present. The peeled seed was planted in cones filled with potting soil. The planted cones were placed in a greenhouse where they germinated under mist. The mist was removed after germination was complete. The seedlings grew in the greenhouse with ample light, heat, and nutrients until their stems have begun to harden and were about 12 inches tall. They were then acclimatized in a lathhouse before being planted in a seedling nursery. At the end of the first growing season, the seedlings were undercut and then planted in high density seedling blocks at the University of California Davis campus research orchards.

Field Testing

Field testing and evaluation of prune selections such as 'G2S-8' are carried out generally at several levels.

Initial testing involves evaluations made in the seedling blocks located at UC Davis and the selections blocks at Parlier, Calif and Winters, Calif. Initial fruit evaluation is made on the original self-rooted seedlings in the high-density seedling blocks. When enough fruit is available on a seedling for preliminary data collection and a positive evaluation results, the seedling becomes a "selection" and is then considered for repropagation in prune selection blocks located in Parlier, Calif and Winters, Calif. Depending on the perceived potential of the individual selection, from two to four trees of any one selection is established on commercial rootstock. Variations in fruit size, tree vigor, maturity date, and other characteristics may and often do, occur when a selection is moved onto a rootstock from the original seedling. All individual selections are re-fruited in the selection blocks prior to advanced testing with growers.

Subsequent testing involves the establishment of advanced selections in grower orchards in various prune growing locations. Again, depending on the perceived value of an individual item, from two to fifty trees of any one selection are established at any one location. Grower tests are established in counties throughout the Sacramento and San Joaquin Valleys in California where prunes are a commercial crop.

Further testing involves the planting of small test acreage, usually of a single targeted selection. The size of these further tests depends on the apparent potential of the individual selection and the level of risk that the cooperating grower wishes to assume. Planting size ranges from twenty-five up to several hundred trees. Commercial value of an item can be established in test markets with the expanded production of this further testing.

Selection and Evaluation

Selection and evaluations begin with the first time the seedlings bloom. The tree is noted for precocity and is checked later to see if it successfully set fruit. When a seedling sets its first sizable crop, the fruit is evaluated in the field setting. Maturity date, tree vigor, crop load, fruit size, fruit color, internal flesh quality, pit size, pit type (cling or free), fresh taste, and external flaws are recorded. During this first evaluation, trees can be discarded on the basis of any of these characteristics, except for crop load which is usually only used as a disqualifier after several years of cropping. Some examples of first year disqualifiers are high acidity or astringency, extremely tight pit, large pit size, split pits, gas pockets, lack of firmness in flesh, green or mottled color, small fruit size, deep sutures, cracks on side or ends, heat damage, russet scab, and early fruit drop.

If the field evaluation of a seedling is positive and the fruit quality shows potential, a sample of ten fruit is collected and a secondary fresh evaluation is done in the laboratory. This evaluation is done on the same day as the field evaluation. The fruit is weighed and the average fruit weight (g) is recorded. The maturity of the fruit is estimated by pressure testing the flesh of the ten fruit and recording the average (PSI). The soluble solids are sampled by taking half of each fruit and pulverizing them together in a blender then examining the clear juice with a refractometer. This method establishes the average soluble solids (Brix) of the sample. Again, taste and any exterior or internal flaws are recorded. If the sample has high soluble solids compared to other samples at that ripening date and the flavor and fruit quality are above average, then a larger sample is collected from the seedling for test drying. If the sample shows low soluble solids or poor fruit quality then the seedling is either marked for discard or evaluation in the next year.

The next step in the evaluation system is to test dry the harvested samples. A dehydrator may be utilized to dry the fruit. The samples are placed in net bags and washed before drying. They are dried for two hours at 185° F. after which the temperature is lowered to 165° F. for the remaining time. Samples are dried between 18 to 24 hours depending on filled drier capacity and individual sample characteristics. The prune samples are weighed before and after drying and the fresh to dry ratio is calculated. The dried fruit count per pound is also recorded. The prune samples are stored at 32° F. until the late fall when the final evaluation takes place.

The last evaluation for the year is the rehydrated or processed evaluation. The prune samples are rehydrated by submerging the fruit in water that is between 185-203° F. for six to eight minutes. The rehydrated prunes are placed in a plastic bag and stored in a refrigerator until their moisture content has equalized. The processed dried plums are evaluated for fruit size, fruit color, color uniformity, surface wrinkles, skin peel, surface brightness, fruit shape, pit size, pit adherence, flesh color, flesh quality, and taste. Taste and appearance play a large role in the advancement of a seedling selection. Items are discarded if any of these traits do not equally compare to or exceed the standards set by the cultivar, 'Improved French'.

The evaluations described above take place at all levels of testing. The emphasis on individual traits changes at each level. In early testing, more emphasis is given to the actual fruit characteristics during the processed evaluation. In later testing the whole tree characteristics are emphasized, such as time of maturity over varying environments, annual bearing habits, crop load, and tree structure.

'UC G2S-8'

As detailed above, 'UC G2S-8' is a high-quality prune (dried plum) with a sweet fruity flavor and thick meaty flesh. It is distinctly different from the industry standard 'Improved French' in fresh and dried fruit flavor and color. This new cultivar has been identified utilizing the above-described selection and evaluation procedure.

The fruit maturity date of 'UC G2S-8' is later than 'Improved French' and harvest begins essentially when commercial 'Improved French' harvest ends. The size of the fruit averages 31 grams fresh weight with an average soluble solids concentration between 22.5 and 28.2 degrees brix. The fruit is oval shape, without a neck. A yellow skin color covers the entire fruit at maturity. The flesh is a golden orange and can retain the golden color after drying. The fruit dries without slabbing or bleeding and the pit remains semi-free. The results of pitting trials show that the pit comes free of the flesh and the processed fruit is of very high eating quality. The shape of the dried fruit is similar to "French".

The harvest data of 'UC G2S-8' in comparison to 'Improved French' are shown in Table 1.

TABLE 1

Harvest Data Summary of 'UC G2S-8' and 'Improved French' grown in Winters, Calif, 3 consecutive years.

| Selection | Date | Days Harvested after 'Improved French' | Crop Load | Size (average grams per fruit) | Soluble Solids (% Brix) |
|---|---|---|---|---|---|
| UC G2S-8 | Sep. 3, 2019 | +7 | Medium | 32 | 22.5 |
| Improved French | Aug. 27, 2019 | | Medium | 19 | 24.4 |
| UC G2S-8 | Aug. 31, 2020 | +7 | Medium to Heavy | 31.7 | 24.8 |
| Improved French | Aug. 24, 2020 | | Medium | 18 | 27.2 |

TABLE 1-continued

Harvest Data Summary of 'UC G2S-8' and 'Improved French' grown in Winters, Calif, 3 consecutive years.

| Selection | Date | Days Harvested after 'Improved French' | Crop Load | Size (average grams per fruit) | Soluble Solids (% Brix) |
|---|---|---|---|---|---|
| UC G2S-8 | Sep. 6, 2021 | +14 | Medium to Heavy | 35 | 28.2 |
| Improved French | Aug. 23, 2021 | | Medium to Heavy | 20.7 | 23.9 |

What is claimed is:

1. A new and distinct cultivar of prune tree designated 'UC G2S-8' substantially as described and illustrated herein.

* * * * *